United States Patent [19]

Stevens

[11] Patent Number: 5,133,844
[45] Date of Patent: Jul. 28, 1992

[54] METHOD OF ELECTRIC FIELD FLOW FRACTIONATION WHEREIN THE POLARITY OF THE ELECTRIC FIELD IS PERIODICALLY REVERSED

[75] Inventor: Fred J. Stevens, Naperville, Ill.

[73] Assignee: United States Department of Energy, Washington, D.C.

[21] Appl. No.: 494,074

[22] Filed: Mar. 15, 1990

[51] Int. Cl.[5] .................... G01N 27/26; B01D 57/02; B03C 5/02
[52] U.S. Cl. ........................... 204/180.1; 204/299 R; 204/186; 204/302; 204/182.1
[58] Field of Search ................ 204/299 R, 180.1, 186, 204/182.1, 302

[56] References Cited

U.S. PATENT DOCUMENTS

| | | | |
|---|---|---|---|
| 3,207,684 | 9/1965 | Dotts, Jr. | 204/299 R X |
| 3,506,554 | 4/1970 | Broome | 204/180.1 |
| 4,440,638 | 4/1984 | Judy et al. | 204/302 X |
| 4,874,507 | 10/1989 | Whitlock | 204/299 R X |
| 5,011,022 | 4/1991 | Palepu et al. | 210/513 X |

OTHER PUBLICATIONS

Wolfgang Thormann et al "Focusing Counterparts of Electric Field Fractionation and Capillary Electrophoresis-Electrical Hyperlayer Field Flow Fractionation and Capillary Isoelectric Focusing" *Journal of Chromatography* 461 (1989) 95-101.
Karin D. Caldwell "Field Flow Fractionation" *Analytical Chemistry*, vol. 60, No. 17 (Sep. 1, 1988) 959A-971A.
Joe M. Davis et al "Retention by Electrical Field-Flow Fractionation of Anions in New Apparatus with Annular Porous Glass Channels" *Analytical Chemistry* vol. 59, No. 9 (May 1, 1987) 1339-1348.
J. Calvin Giddings "Field Flow Fractionation" *Chemical & Engineering News* (Oct. 10, 1988) 34-45.
J. Calvin Giddings "Field-Flow Fractionation-Extending the Molecular Weight Range of Liquid Chromatography to One Trillion ($10^{12}$)" *Journal of Chromatography* 125 (1976) 3-16.
J. Calvin Giddings "Transport, Space, Entropy, Diffusion, and Flow-Elements Underlying Separation by Electrophoresis, Chromatography, Field-Flow Fractionation and Related Methods" *Journal of Chromatography* 395 (1987) 19-32.
Karin D. Caldwell "Electric Field-Flow Fractionation of Proteins" *Science*, vol. 176 (Apr. 21, 1972) 296-298.

*Primary Examiner*—John Niebling
*Assistant Examiner*—John S. Starsiak, Jr.
*Attorney, Agent, or Firm*—Hugh W. Glenn; Robert J. Fisher; William R. Moser

[57] ABSTRACT

A novel method of electric field flow fractionation for separating solute molecules from a carrier solution is disclosed. The method of the invention utilizes an electric field that is periodically reversed in polarity, in a time-dependent, wave-like manner. The parameters of the waveform, including amplitude, frequency and wave shape may be varied to optimize separation of solute species. The waveform may further include discontinuities to enhance separation.

17 Claims, 15 Drawing Sheets

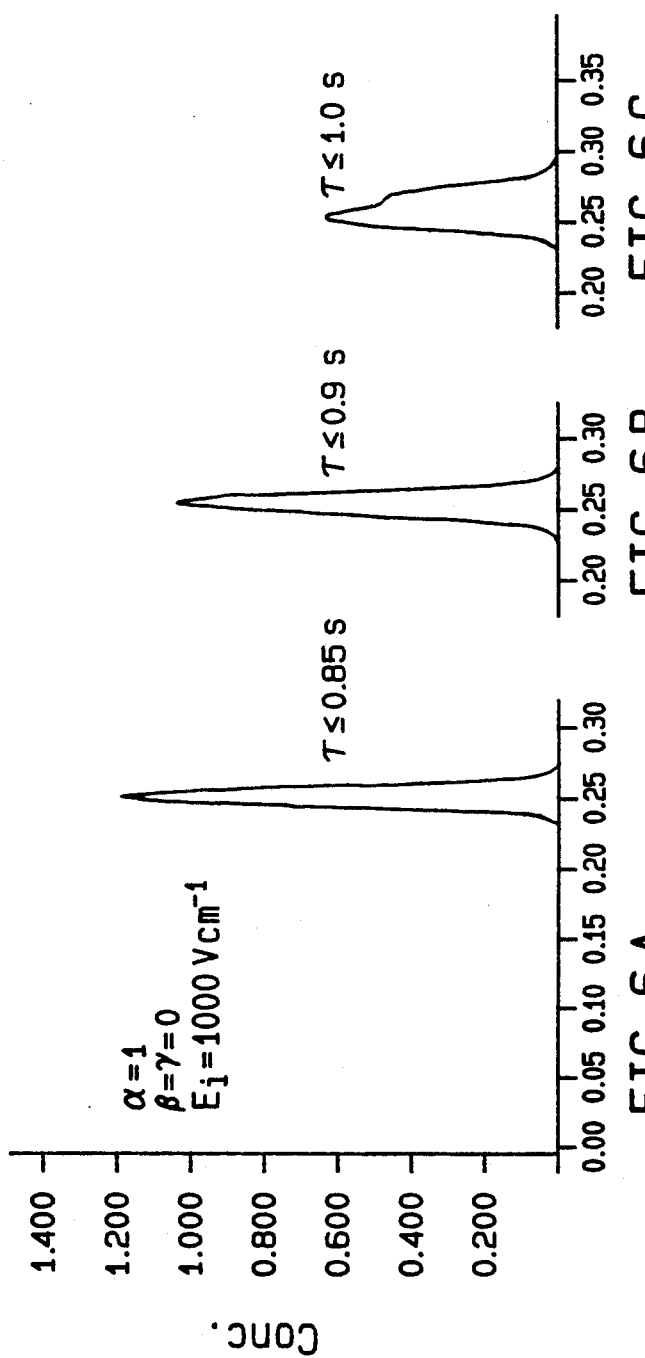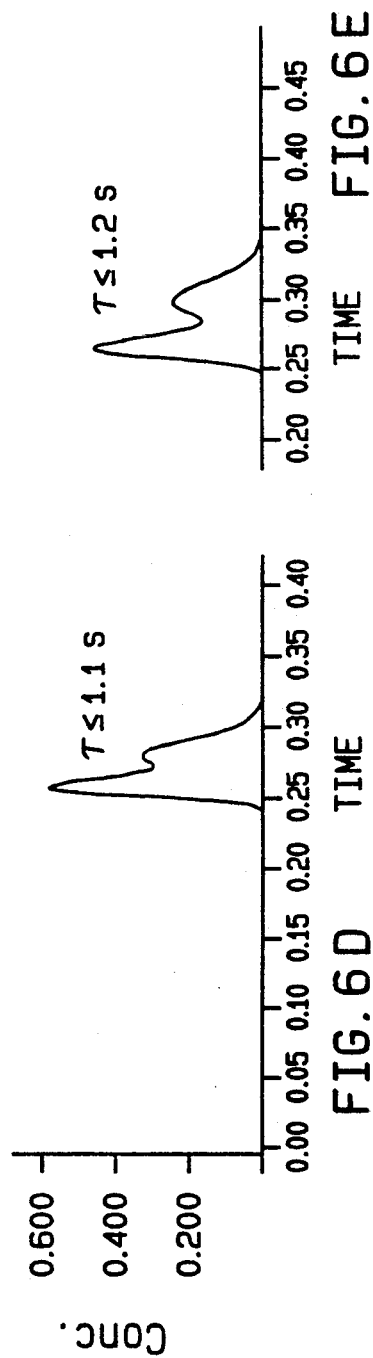

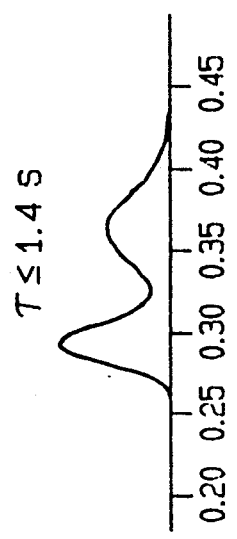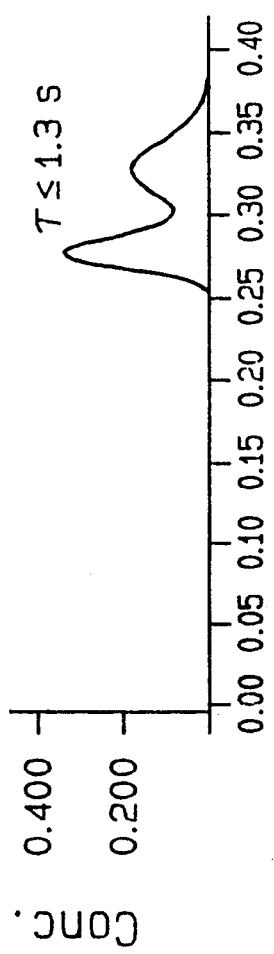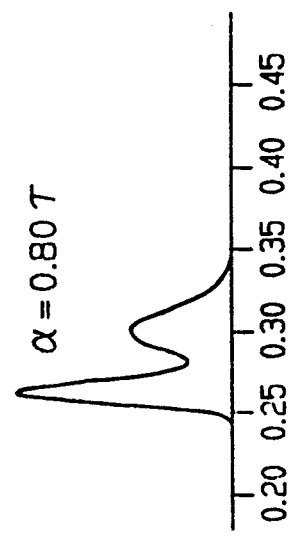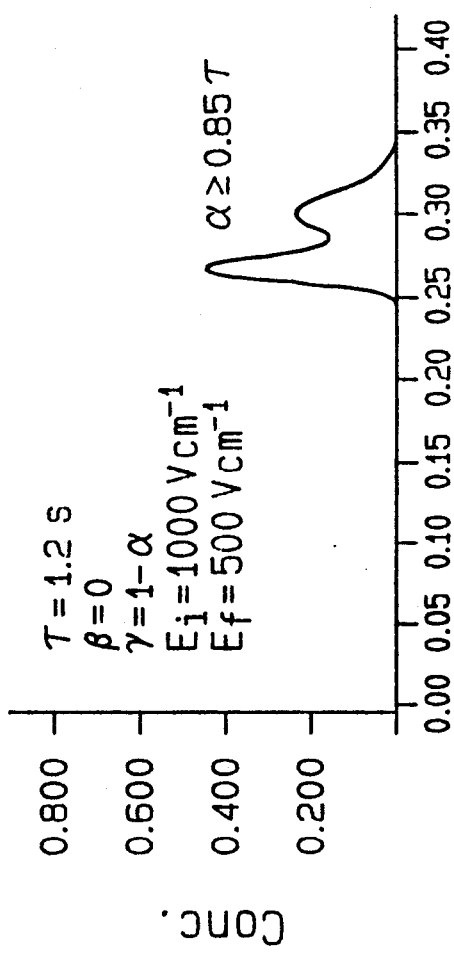

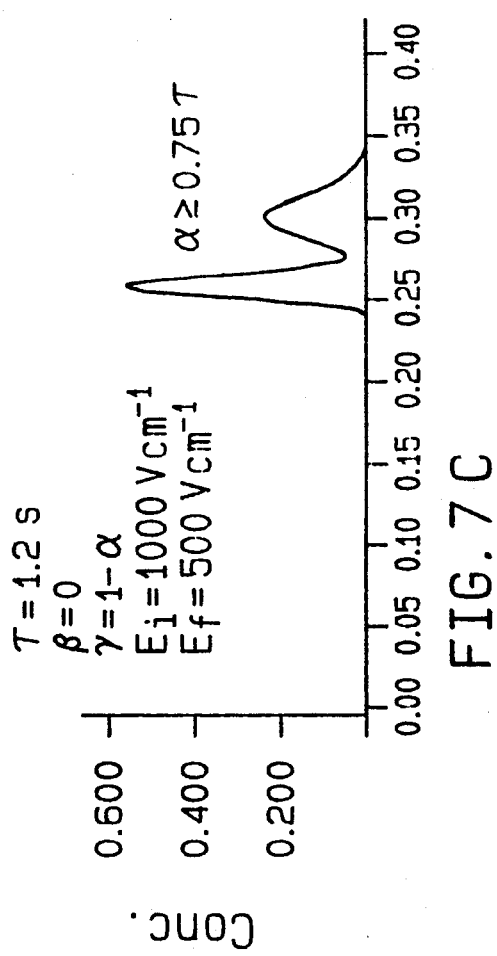
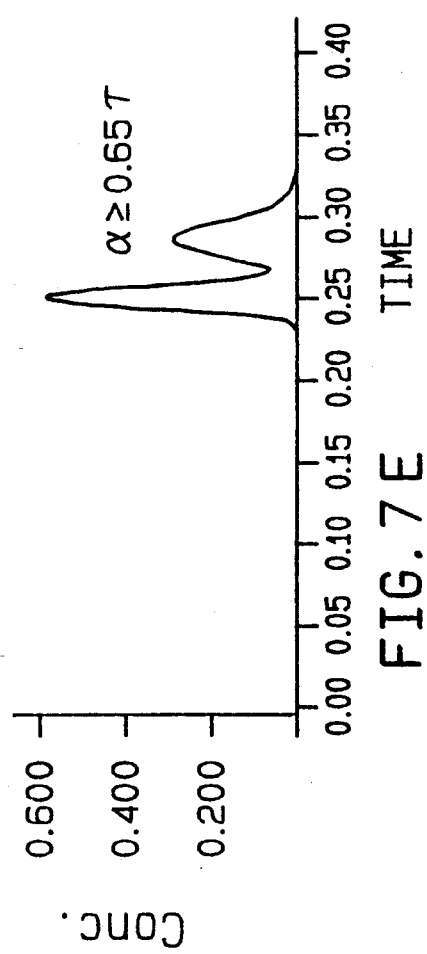
FIG. 7C  FIG. 7D  FIG. 7E  FIG. 7F

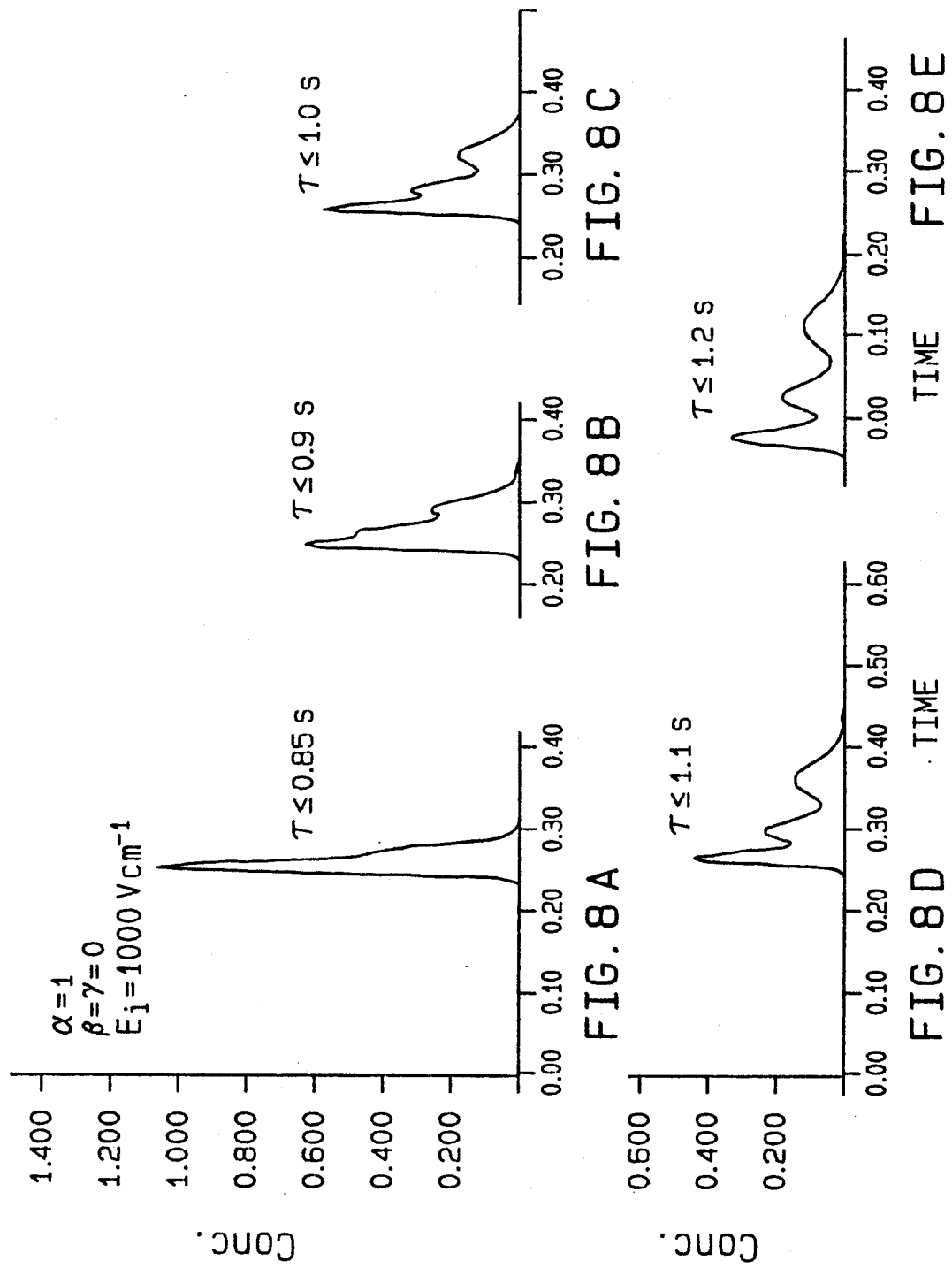

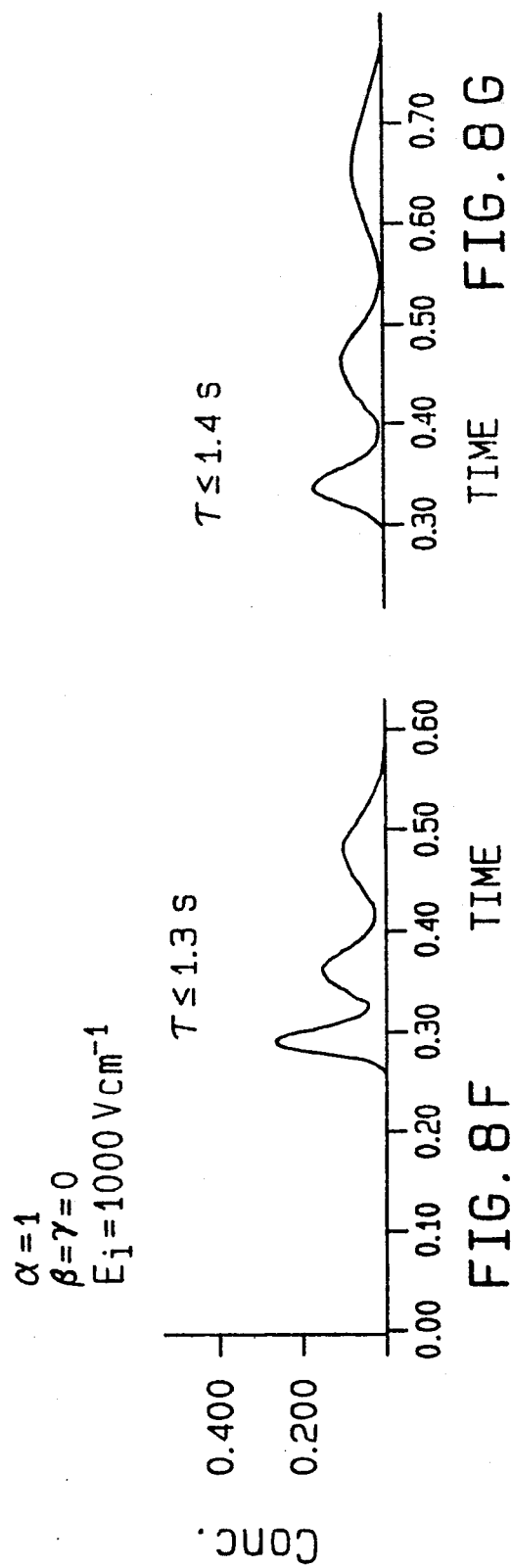

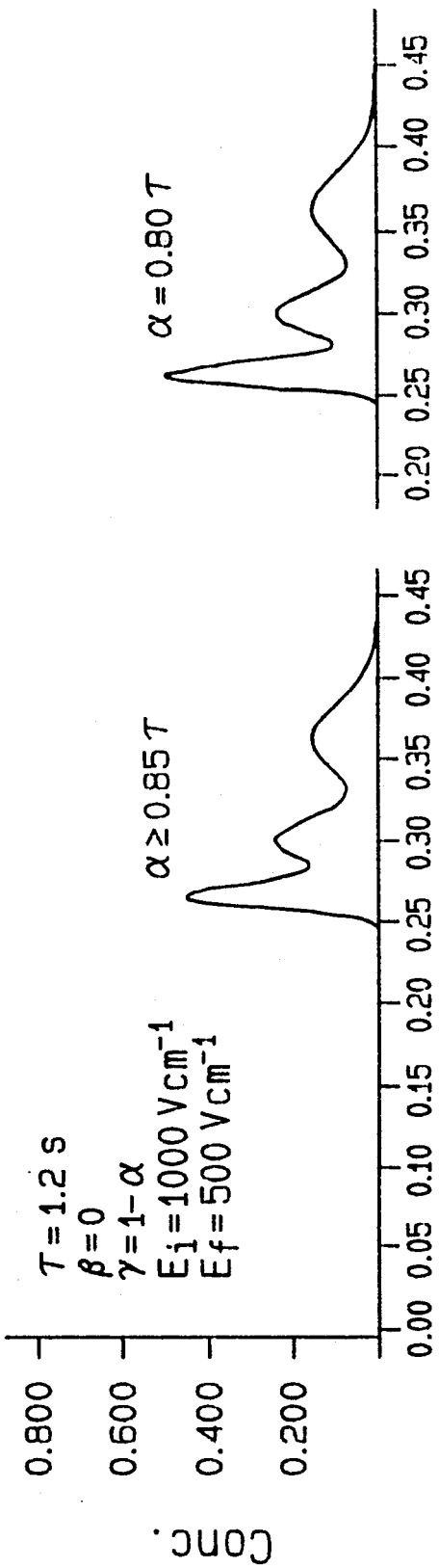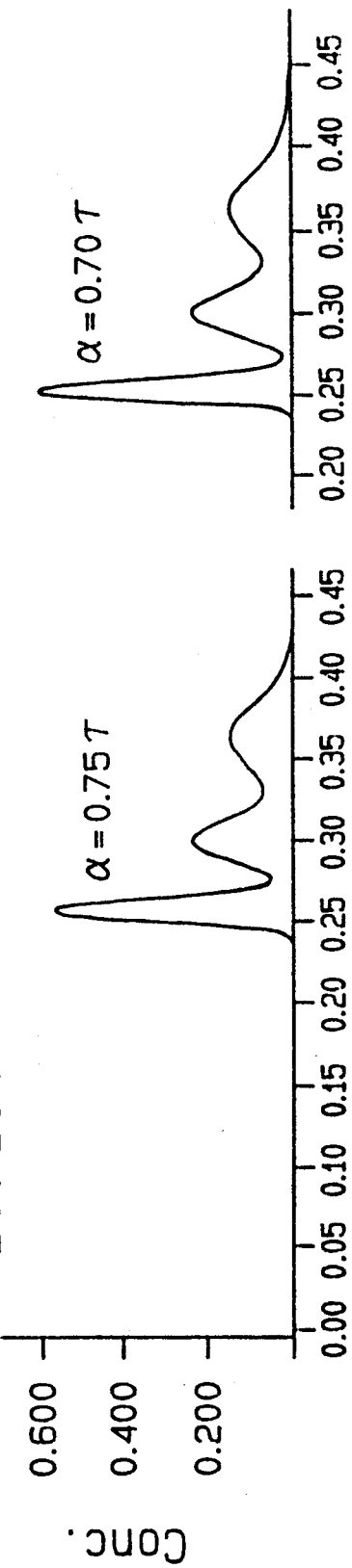
FIG. 10 A
FIG. 10 B
FIG. 10 C
FIG. 10 D

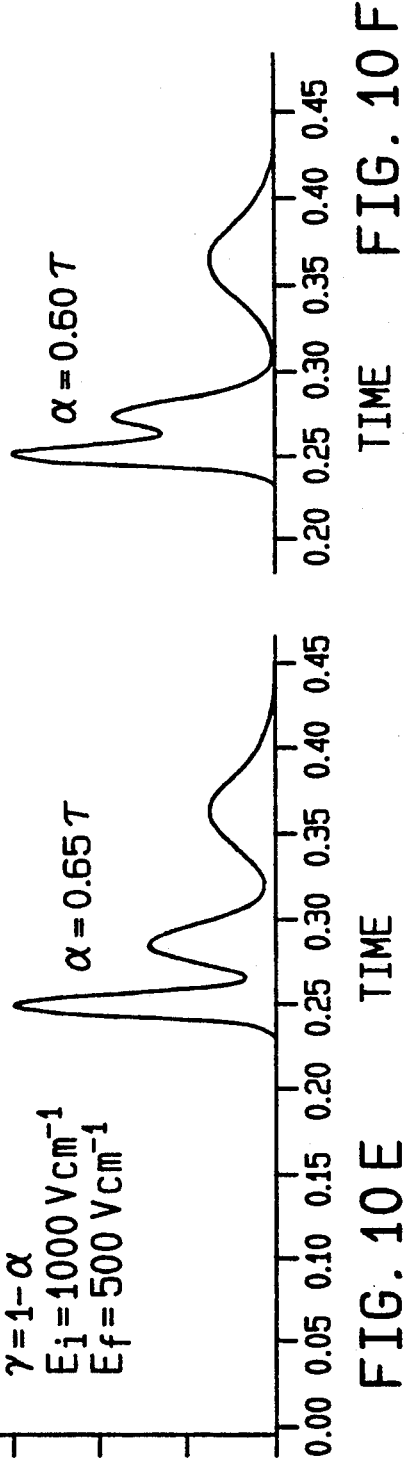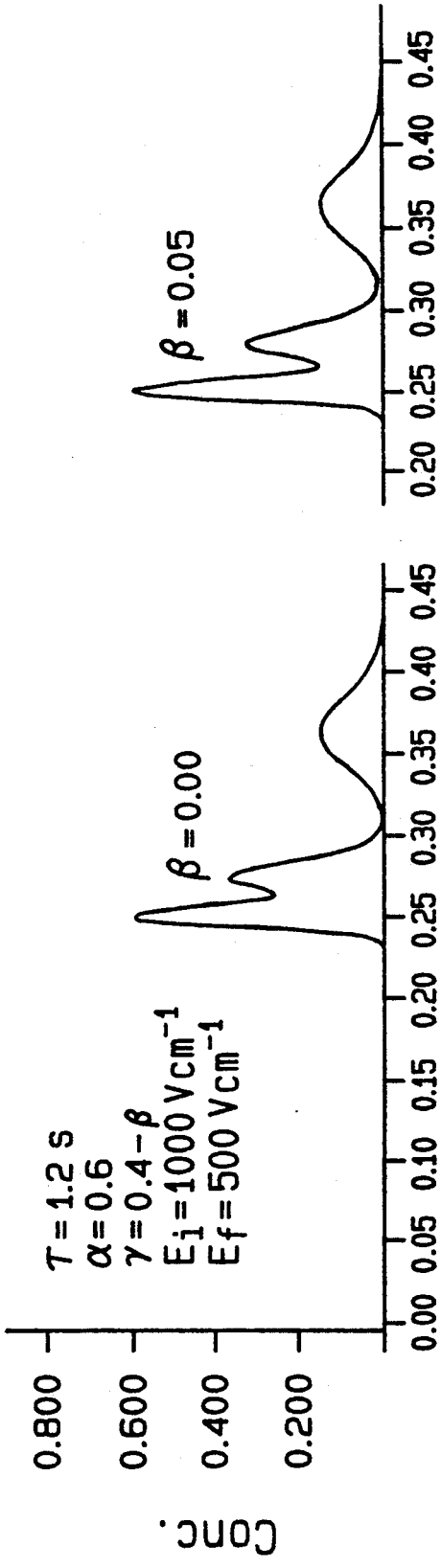

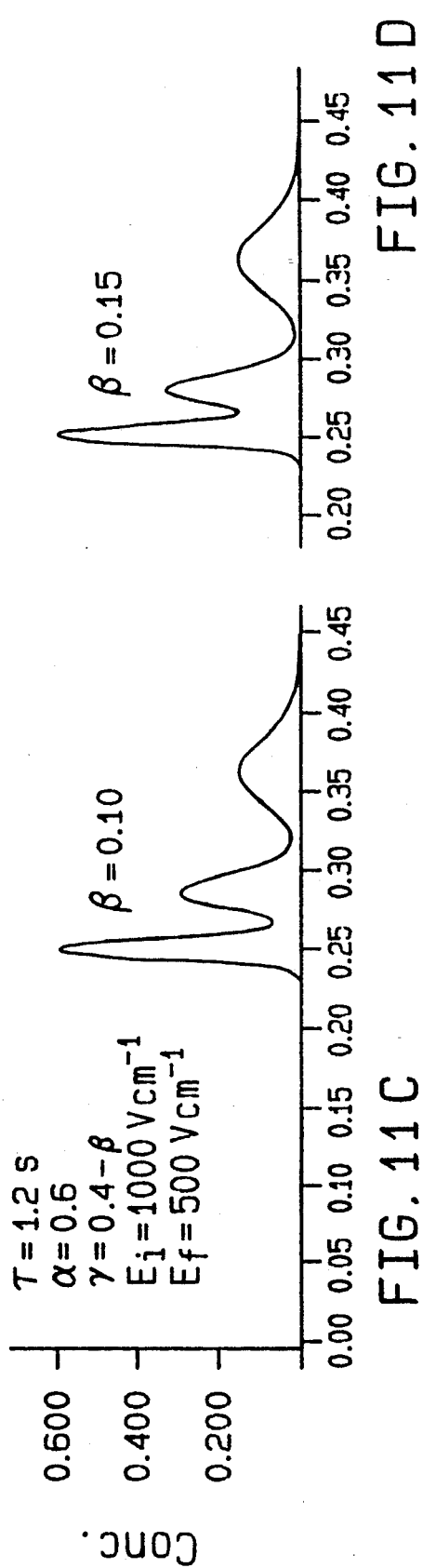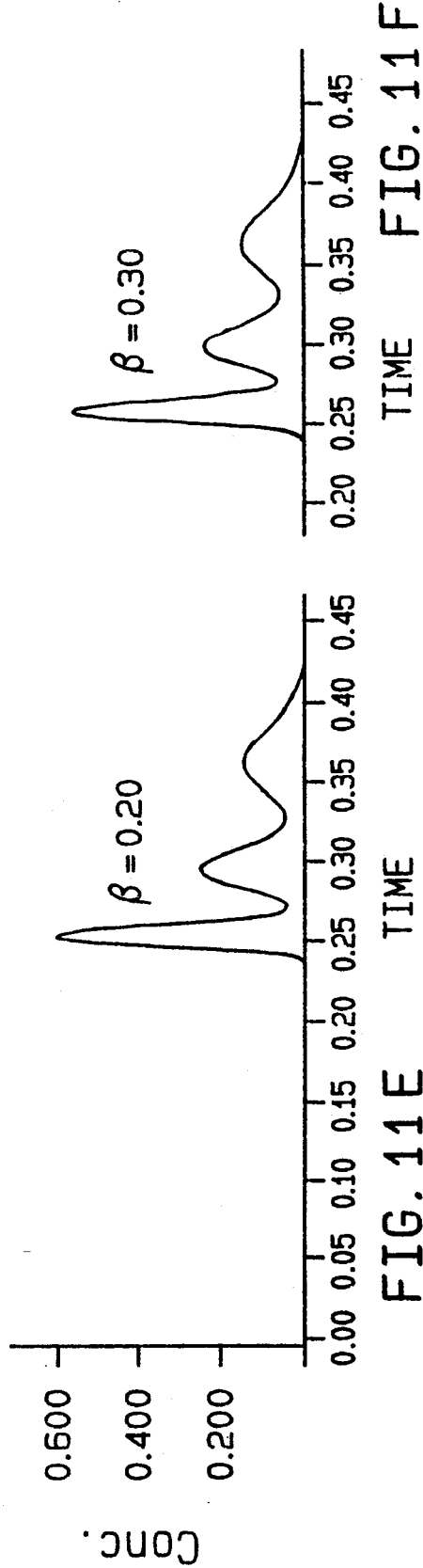
FIG. 11C  FIG. 11D  FIG. 11E  FIG. 11F

METHOD OF ELECTRIC FIELD FLOW FRACTIONATION WHEREIN THE POLARITY OF THE ELECTRIC FIELD IS PERIODICALLY REVERSED

CONTRACTUAL ORIGIN OF THE INVENTION

The United States Government has rights in this invention under Contract No. W-31-109-ENG-38 between the U.S. Department of Energy and Argonne National Laboratory.

BACKGROUND OF THE INVENTION

The present invention relates generally to field flow fractionation technology and more particularly to a method of electric field flow fractionation wherein the polarity of the electric field is periodically reversed in accordance with a time-dependent waveform.

Field flow fractionation, a method obtaining high resolution separations of organic and inorganic colloids and soluble molecules, has been known in the art for approximately twenty years. The term "field flow fractionation" uses the word "field" in a generic sense. The "field" may comprise an electric field, a temperature gradient, a pH gradient, gravitational sedimentation or sedimentation through the application of a centrifugal force. The field is made to act upon a flowing solution or colloidal suspension and causes segregation or fractionation of the solute molecules or colloid particles. It will be understood by those skilled in the art that while the following discussions are directed at solutions, many of the same principles apply to colloidal suspensions.

In field flow fractionation, a solution, having solute molecules dissolved therein, is made to flow through a working chamber formed in a fractionating conduit. Fluid flow in the working chamber is generally laminar in nature. The solute species is added in a concentrated form to a carrier solvent that is already present in and flowing through the working chamber.

Usually, the construction of the working chamber is capillary in nature, i.e., having relatively small and generally uniform transverse cross-sectional dimensions in comparison to its axial length. The working chamber may have a simple cylindrical shape or may be of a generally rectangular cross-sectional configuration. In the case of a rectangular cross-sectional configuration, the working chamber has a depth substantially smaller than its width, so that solution flow through the working chamber is in the form of a thin layer.

Under conditions of laminar fluid flow in a fractionating conduit, the flow velocity of any given fluid particle through the working chamber is a function of the distance of the fluid particle from the conduit wall. The velocity of a given fluid particle ranges from a maximum at a position midway between opposing conduit walls to a theoretical minimum of zero at the conduit wall. Thus, in the case of a rectangular working chamber, laminar fluid flow exhibits a velocity profile in the shape of a parabolic curve, the greatest velocity being at the transverse midpoint of the chamber. This velocity profile of the laminar fluid flow is advantageously used with the desired "field" to selectively separate or fractionate solute molecules from the flowing carrier solvent in the working chamber.

Although fractionating conduits of various shapes have been employed, those having a rectangular working chamber are most easily adapted for use with an electric field. The fractionating conduit is constructed to include a pair of parallel electrical conductor plates, separated by a pair of thin electrical insulator elements, which form the sidewalls of the conduit. Application of a voltage across the conductor plates generates an electric field in the working chamber that is substantially orthogonal to the direction of laminar solution flow.

The concentrated solution of solute molecules is injected into the flowing carrier solvent at an input end of the working chamber. The solute is carried through the conduit by the carrier solvent and the electric field creates a driving force on the solute molecules, causing them to migrate toward one of the conductor plates.

The solute molecules are removed from a discharge end of the working chamber, with the carrier solvent. As a consequence of the differential in electrophoretic mobilities of the solute species, the differing solute species move back into the mobile zone of the carrier solvent at differing rates Thus, the differing solute species are subjected to differing rates of axial transport and the concentration of each solute species in the carrier solvent exhibits a Gaussian distribution as a function of time when measured at the discharge end of the fractionating conduit.

In field flow fractionation numerous parameters have been varied in attempts to improve the results obtained therefrom. For instance, the rate of laminar flow of the carrier solution can be programmed in a time-dependent, variable manner. Such programmed solution flow rates may be used to obtain better separation of the concentration peaks of the fractionated solute species at the discharge end of the fractionating conduit.

It will be understood by those skilled in the art that several different types of "fields" may be combined in a single fractionating system to enhance separation. However, the prior use of electric fields in field flow fractionation is of particular interest with respect to the present invention. While solution flow velocity, pH and thermal gradients and sedimentation forces can, to some extent, be programmed in a time-dependent format, such programming generally requires quite complicated control devices. Electric fields, however, can be easily regulated or programmed in a time-dependent manner with equipment that is already well known in the art. In prior art electric field flow fractionating systems, electric field strength has been programmed as a function of time in a linear manner, and in manners which include combined linear and step functions, parabolic functions (with and without time delays) and exponential decay functions (with and without time delay) to enhance separation of the desired solute molecules from the flowing carrier solvent.

In prior art field flow fractionation methods, regardless of the "field" employed, the field is used to cause solute molecules to migrate toward one interior wall of the fractionating conduit where the theoretical axial velocity of the carrier solvent is zero. Thereafter, the differential rates of axial movement of differing solute species through the fractionating conduit and the ultimate fractionated discharge, depend primarily upon inherent differences in the diffusion rates, densities, etc., of the solute molecules. Thus, it is frequently difficult to purify or fractionate solute molecules having similar diffusion rates in the given carrier solvent or similar molecular weights or densities. Effective and efficient fractionation is particularly important but often difficult to achieve in the fields of biology and genetic engineering, where it is desirable to separate multiple compositions of macromolecules, such as nucleic acid fragments.

OBJECTS AND SUMMARY OF THE INVENTION

It is therefore an object of the present invention to provide an improved method of electric field flow fractionation for fractionating solute molecules.

It is another object of the present invention to provide an improved method of electric field flow fractionation, wherein the electric field has at least one vector component orthogonal to the direction of laminar solution flow and wherein the polarity of the electric field is periodically reversed in a time-dependent manner.

It is another object of the present invention to provide an improved method of electric field flow fractionation wherein the polarity of the electric field is periodically reversed in a time-dependent manner which constitutes a waveform, and wherein the parameters of the waveform may be varied to achieve improved separation of solute species in the carrier solution at the discharge end of the fractionating conduit.

Yet another object of the present invention is to provide a method of electric field flow fractionation wherein the polarity of the electric field is varied in a time-dependent, wave-like manner and the method is compatible with other types of field flow fractionation which utilize fields such as centrifugal force, gravity, thermal gradients, pH gradients and the like.

Still another object of the present invention is to provide an improved method of electric field flow fractionation for fractionating solute molecules wherein the solute molecules are of the type generally referred to as biological macromolecules.

The present invention overcomes the difficulties associated with prior art field flow fractionation by employing an electric field having at least one vector component orthogonal to the direction of laminar solution flow, and by varying the polarity of the electric field in a time-dependent, waveform manner. The amplitude, periodicity, and shape of the waveform may all be varied as functions of time to obtain better separation of differing solute species.

Because the polarity of the electric field is periodically reversed, solute molecules repeatedly traverse the working chamber of the fractionating conduit in directions corresponding to the electric field (i.e., transverse to the longitudinal axis of the chamber and the direction of carrier solution flow). During such transverse transport, the solute molecules are also carried in the direction of the carrier solvent flow, that is in the axial direction of the chamber. The carrier solvent has a parabolic flow velocity profile within the working chamber, wherein the flow velocity of the carrier solvent is theoretically zero at the fractionating conduit wall. Therefore, axial transport of a given solute species at that location is negligible, being substantially limited to that provided by transient diffusion into the mobile solvent zone. If the period of the electric field waveform is relatively long as compared to the time required for transverse solute transport, solute species are fractionated and eluted from the discharge end of the working chamber in an order inversely related to the electrophoretic mobility of the solute species. Conversely, if the period of the electric field waveform is relatively short as compared to the time required for transverse solute transport, solute species are separated and eluted at the discharge end of the working chamber in an order directly related to the electrophoretic mobility of the solute species. Thus, the parameters of the electric field waveform can be adjusted to obtain improved separation of solute species.

The method of the present invention is particularly useful for the purification of solute species such as nucleic acid fragments, which are not amenable to efficient separation or purification via prior art techniques.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIGS. 2A through 2F represent sequential, fragmentary cross-sectional views of the working chamber of the fractionating conduit shown in FIG. 1B, taken along line 2—2 and in the direction of carrier solvent flow;

FIGS. 6A through 6G, FIGS. 7A through 7F, FIGS. 8A through 8G, FIGS. 9A through 9E, FIGS. 10A through 10F and 11A through 11F are simulated fractograms generated by computer simulation of the fractionation method of the invention wherein various parameters of the electric field waveform have been varied.

DETAILED DESCRIPTION OF THE INVENTION

Figure 1A:
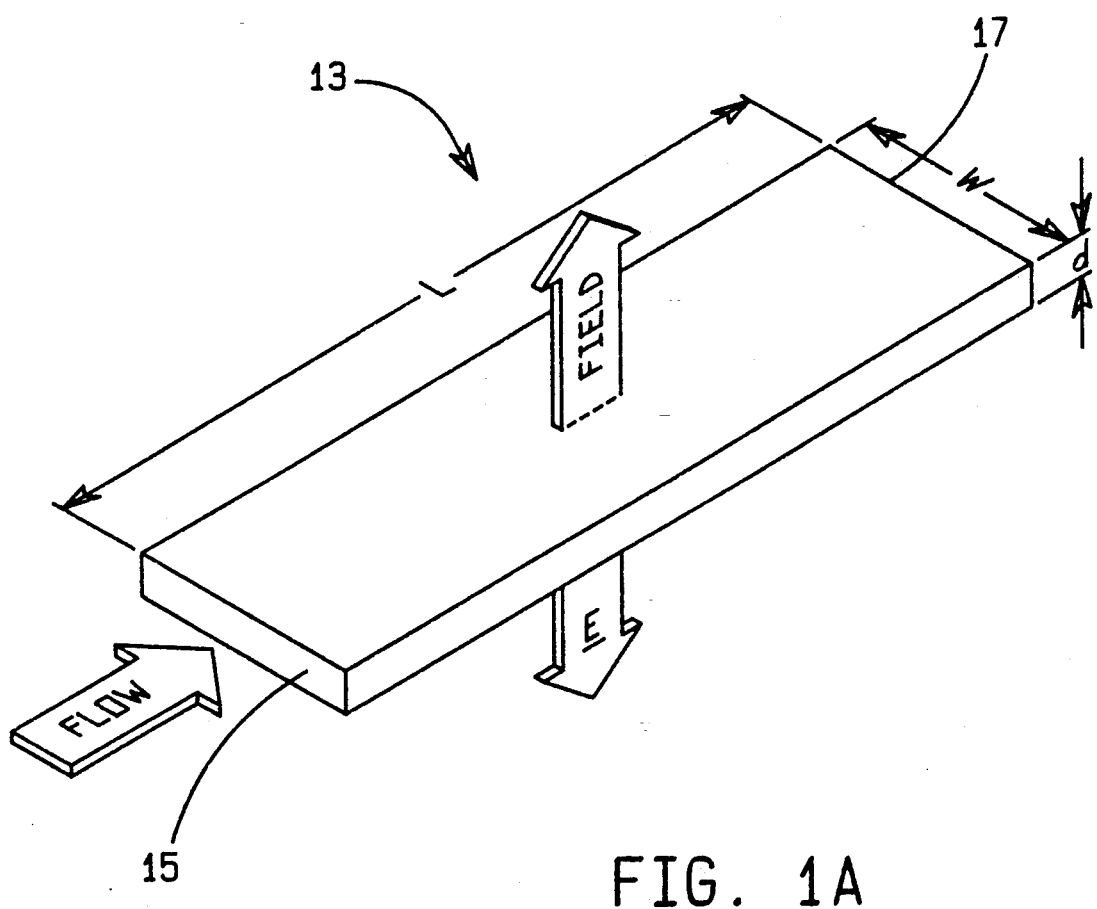
FIG. 1A is a schematic illustration of a preferred geometry of a working chamber in a fractionating conduit, adapted for practice of the fractionation method of the present invention.

Referring now to the drawings, and in particular to FIG. 1A, there is schematically illustrated a preferred geometry of a working chamber in a fractionating conduit, generally indicated by reference numeral 13. It is known in the art that optimal separation of solute species in field flow fractionation may be achieved via laminar flow of a carrier solvent in thin layers or through a capillary conduit. The illustrated geometry of the working chamber 13 is configured so as to have a predetermined axial length L and a substantially uniform, rectangular cross-sectional configuration of predetermined width, W and predetermined depth, d. In accordance with the invention, the working chamber 13 includes an input end 15 into which solute molecules and a carrier solvent are introduced, and a discharge end 17 from which the fractionated solute molecules and carrier solvent are removed. Flow of the carrier solvent through the working chamber 13 is then substantially in the axial direction as indicated by the flow arrow. An electric field, E, having at least one vector component orthogonal to the direction of solution flow, is applied across the working chamber 13. The polarity of the electric field E is periodically reversed in a time-dependent manner having waveform characteristics, as explained hereinafter. The amplitude, periodicity, and shape of the waveform are varied and related to the dimensions of the working chamber, the electrophoretic mobilities of the solute species and the rate of carrier solvent flow to optimize separation or fractionation of solute species.

Figure 1B:
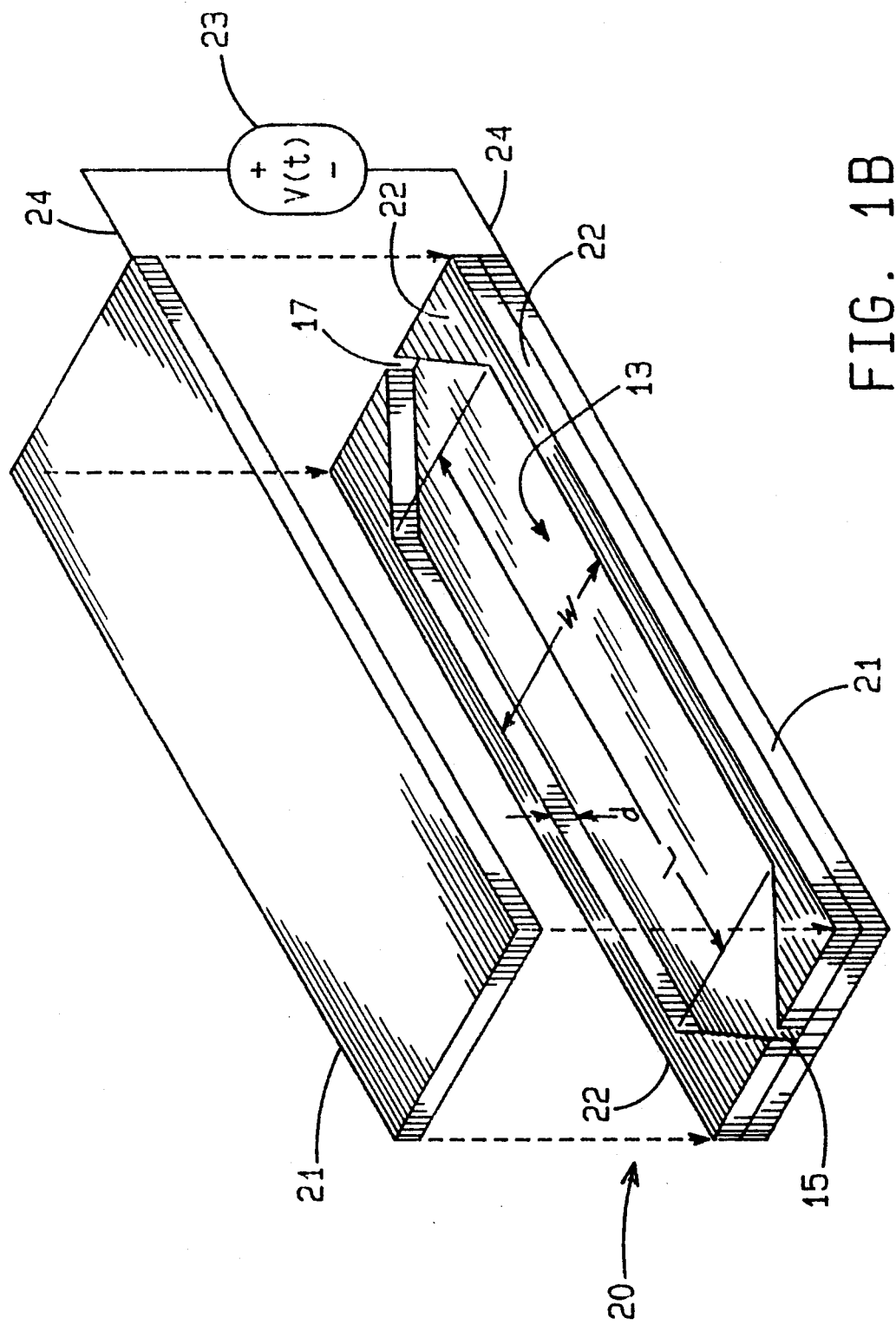
FIG. 1B is a perspective, exploded view of a fractionating conduit adapted for application of an electric field in a direction normal to the direction of carrier solvent flow and having a working chamber geometry in accordance with that illustrated in FIG. 1A.

FIG. 1B shows one construction of a fractionating conduit 20 which has a working chamber 13 of the preferred geometry illustrated in FIG. 1A. The fractionating conduit 20 includes a pair of parallel electrical conductor plates 21 separated by a pair of thin electrical insulator elements 22, which form the sidewalls of the fractionating conduit 20. A programmable, alternating voltage source 23 has a pair of terminals 24 in respective electrical communication with conductor plates 21. The application of a voltage across conductor plates 21 causes the fractionating conduit 20 to function in the manner of a capacitor, so that an electric field E (as illustrated in FIG. 1A) is established between plates 21. The direction of electric field E is, of course, normal to the direction of carrier solvent flow (from input end 15 to discharge end 17) regardless of the polarity of the voltage delivered by voltage source 23. The strength of the electric field E in the working chamber 13 then depends upon the magnitude of the voltage delivered by voltage source 23 and the dielectric constant of the carrier solution contained therein.

It will be understood by those skilled in the art that although the electric field E is present in the converging and diverging ends of the working chamber in the illustrated embodiment of the fractionating conduit 20 (adjacent input end 15 and discharge end 17) the effect of this end configuration upon fractionation is negligible and can be ignored.

It will also be understood that electrical conductor plates 21 and electrical insulator elements 22 are fabricated from materials or treated with coatings that are substantially chemically inert in the presence of the desired carrier solvent and solute species so that chemical contamination of the fractionated solutes is avoided.

Figure 2A:
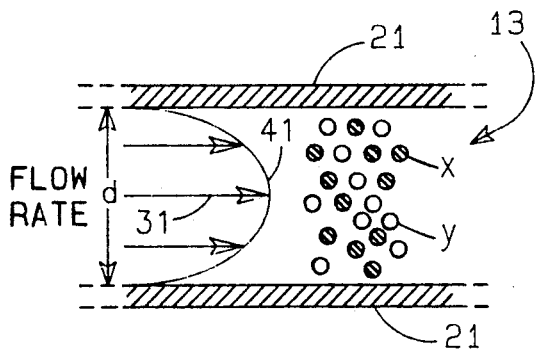
FIGS. 2A through 2F are sequential, schematic representations of the separation or fractionation of two different, hypothetical solute species, carried out in accordance with the method of the present invention wherein the frequency of the reversal of the electric field is relatively slow.

Referring now to FIGS. 2A through 2F, there is schematically illustrated, on a molecular level, fractionation of two hypothetical species of chemical solutes X and Y, in accordance with the invention. FIG. 2A illustrates the random distribution of solute species X and Y in the working chamber 13, at a time prior to the application of any electric field E. Solute species X and Y are in solution with a carrier solvent 31, having been injected into the working chamber 13 in concentrated form near the input end 15 of the fractionating conduit 20.

Because carrier solvent 31 flows between conductor plates 21 under conditions of laminar flow, the flow rate, or the velocity of carrier solvent 31 follows a parabolic profile as illustrated at 41. The flow rate of a given fluid particle is theoretically zero adjacent either plate 21 and at a maximum a distance d/2 from the plates 21.

Figure 2B:
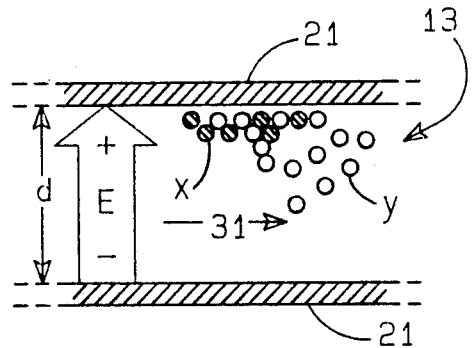

FIG. 2B illustrates the initial reaction of solute species X and Y upon the application of an electric field E. Because X and Y have differing electrophoretic mobilities in the carrier solvent 31, X and Y migrate toward one of the conductor plates 21 at different rates. In the illustration of FIGS. 2A-2F, chemical solute X is represented as having a greater electrophoretic mobility in carrier solvent 31 than chemical species Y. Species X therefore migrates toward electrical conductor plates 21 at a faster rate than chemical species Y. Consequently, chemical species Y has a longer residence time in the mobile flow region of the solvent 3 and undergoes further axial transport than species X.

Figure 2C:
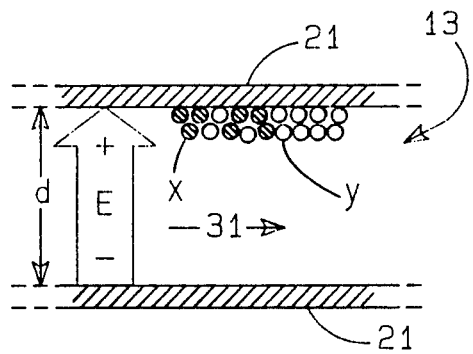

FIG. 2C represents the state of X and Y at some time after initial application of the electric field E. FIG. 2C shows that if the field E is applied in one direction for a long enough time, substantially all of species X and Y will have migrated toward one of the electrical conductor plates 21. Nonetheless, separation or fractionation of species X and Y has started to occur.

Figure 2D:
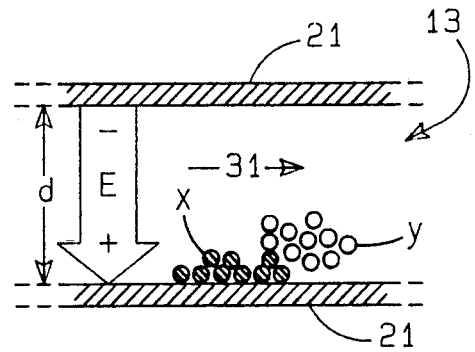
Figure 2E:
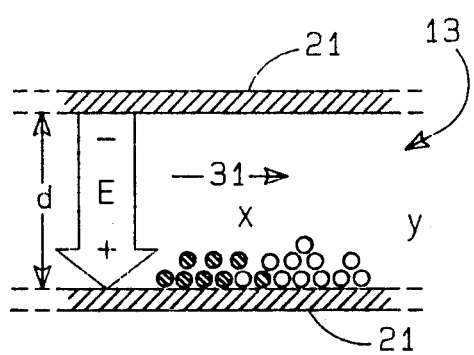

In FIG. 2D, the polarity o the electric field E has been reversed, causing chemical species X and Y to migrate toward the opposite conductor plate 21. Again, because chemical species X has a greater electrophoretic mobility in carrier solvent 31 than does Y, the migration of X to the opposite electrical conductor plate 21 occurs more rapidly for species X than Y. Thus, solute species X becomes "pinned" in the theoretical zero flow velocity zone adjacent conduit wall 21 before specimen Y and segregation of species X and Y further increases as shown in FIG. 2D. At some time later as represented in FIG. 2E, species Y has now completed its transverse migration toward conduit wall 21 and is "pinned" there as well, but ahead of X in the direction of carrier solvent flow.

Figure 2F:
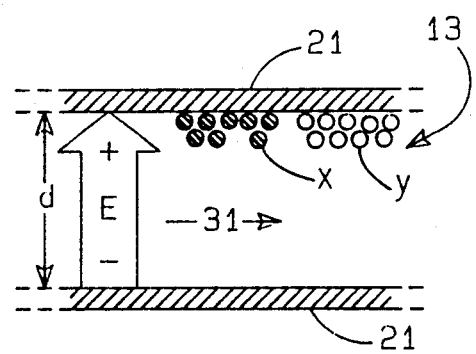

In FIG. 2F, the polarity of electric field E has once again been reversed and applied for a period of time sufficient to permit the migration of both species X and Y to the area of theoretical zero flow velocity of carrier solvent 31. FIG. 2F shows that virtually complete segregation or fractionation of solute species X and Y, within the working chamber 13, has now occurred.

It is important to note that in FIGS. 2A through 2F, the electric field E was applied at a strength and for a time sufficient to permit substantially complete migration of both chemical species X and Y to the appropriate conductor plate 21, prior to reversal of the polarity of the electric field E. The distance, d, separating electrical conductor plates 21, the laminar flow velocity of the carrier solvent 31 and the strength and duration of the electric field E, prior to polarity reversal, may be related to the electrophoretic mobilities of the chemical species X and Y, such that the chemical species exhibiting the lowest electrophoretic mobility, Y is fractionated ahead of the species exhibiting higher electrophoretic mobility, X. Repetitive reversals of the polarity of electric field E, over identical periods of time, causes further fractionation of species X and Y until the species are carried to the discharge end 17 of working chamber 13 and discharged or eluted therefrom in the order described.

Because species Y is fractionated ahead of species X, it is first discharged or eluted from the working chamber 13. When discharged under conditions of a constant flow rate, the respective concentrations of chemical species X and Y in carrier solvent 31, measured as functions of time, yield Gaussian distributions for each species.

Referring now to FIGS. 3A through 3F, there is schematically illustrated another method of fractionation in accordance with the present invention. The illustrations in FIGS. 3A-3F employ the same two hypothetical chemical species X and Y, wherein the electrophoretic mobility of X is greater than Y. In FIGS. 3A through 3F, the electric field E is, however, applied and reversed in such a manner that fractionation takes place in a zone adjacent only one of the conductor plates 21. That is to say, the polarity of the electric field is reversed before complete transverse migration of the solute species to the opposite conductor plate 21 can occur. Thus, the relevant carrier solution flow rate profile 41 is illustrated only in the relevant zone in FIG. 3A.

Figure 3A:
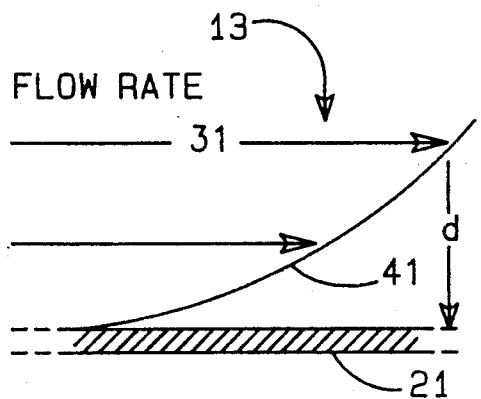
FIGS. 3A through 3F are sequential, schematic illustrations identical to FIGS. 2A through 2E but wherein the frequency of the reversal of the electric field is relatively rapid.
Figure 3B:
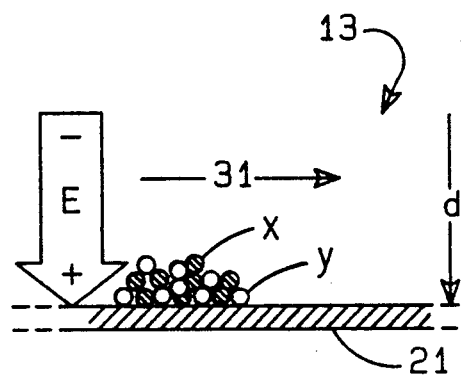

In FIG. 3B, the electric field E is first applied at a strength and for a duration sufficient to cause substantially complete migration of both solute species X and Y to the essentially zero velocity carrier solvent flow region, adjacent one of the conduit walls 21. Thus, the solute species X and Y may be said to be "focused" by this procedure. It should be noted that in the initial "focusing" step, species X and Y are randomly distributed in the carrier solvent 31, at the conduit wall 21.

Figure 3C:
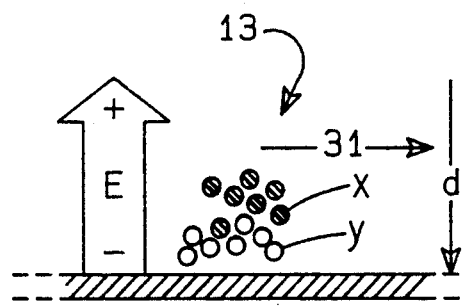
Figure 3D:
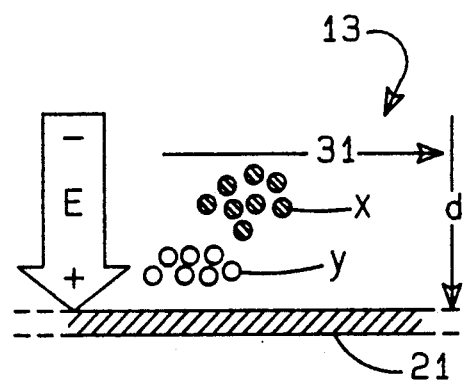
Figure 3E:
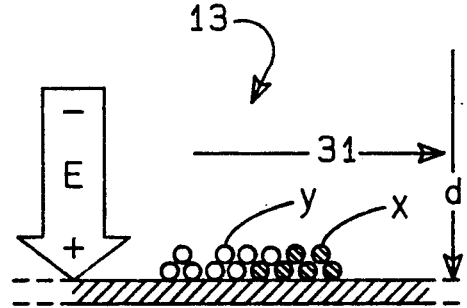
Figure 3F:
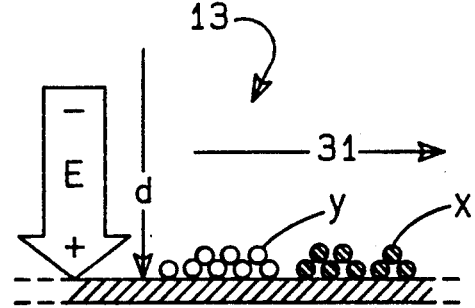

In FIG. 3C, the polarity of the electric field E has been reversed and accordingly, species X enters the higher velocity zone of the carrier solvent 31 at a rate faster than does species Y. In FIG. 3D, the polarity of the electric field E is again reversed, at a time *before* either species X or Y has undergone transverse migration to the opposite conduit wall (not shown). The polarity of the electric field is permitted to remain in this direction until the transverse migration of both species X and Y has caused their return to the theoretically zero axial velocity flow zone of the carrier solvent adjacent the conduit wall 21 (FIGS. 3E and 3F).

Even though the total time allotted for transverse migration of both species X and Y is identical, the greater electrophoretic mobility of solute species X causes it to undergo greater transverse transport than solute species Y. Hence, solute species X is carried into the carrier solvent zone of greater velocity during that time interval. Species X is therefore carried further downstream in the axial direction than species Y. As can be seen, segregation of species X and Y still occurs but species X, having the higher electropheric mobility is eluted ahead of species Y.

FIGS. 2A through 2E and FIGS. 3A through 3E, therefore illustrate that, for a working chamber 13 of given dimensions and a given carrier solvent flow rate, control of the waveform of the periodically reversing electric field can be used to control the segregation or fractionation and elution pattern of chemical species having differing electrophoretic mobilities.

SIMULATION OF ELECTRIC FIELD FLOWFRACTIONATION WITH A PERIODIC REVERSAL OF FIELD POLARITY

The fractionation method of the present invention was verified by employing computer simulation. A computer algorithm was used to generate "simulated fractograms", i.e., graphs of solute concentrations in a carrier solvent as a function of time and as eluted from the discharge end of a fractionating conduit having a working chamber of stipulated dimensions. A typical carrier solvent, flow rate and solute species having electrophoretic mobilities typical of proteins were postulated. The parameters of the waveform of the periodically reversed electric field were varied and the effects of the variation on the elution pattern as embodied in the simulated fractograms were observed.

For purposes of the computer simulated fractograms, a fractionating conduit 20 having a working chamber 13 with a rectangular cross-sectional configuration as illustrated in FIGS. 1A and 1B, was assumed. The chamber 13 was stipulated to have a depth, d, of 0.05 centimeters, a width, W, of 1 centimeter and an axial length, L, of 20 centimeters. Thus, each centimeter of axial length in the working volume 13 represented a volume of 50 microliters.

A programmable voltage source, 23, capable of delivering a peak voltage of 4,500 volts across conductor plates 21 was also assumed. Thus, the strength of the electric field, E, within the working chamber 13 was calculated as follows:

$$E = \frac{V}{d \cdot \epsilon}$$

where V=voltage, d=working chamber depth and $\epsilon$=the dielectric coefficient of the carrier solvent which was assumed to have a value equal to that of water, 89.

Figure 4:
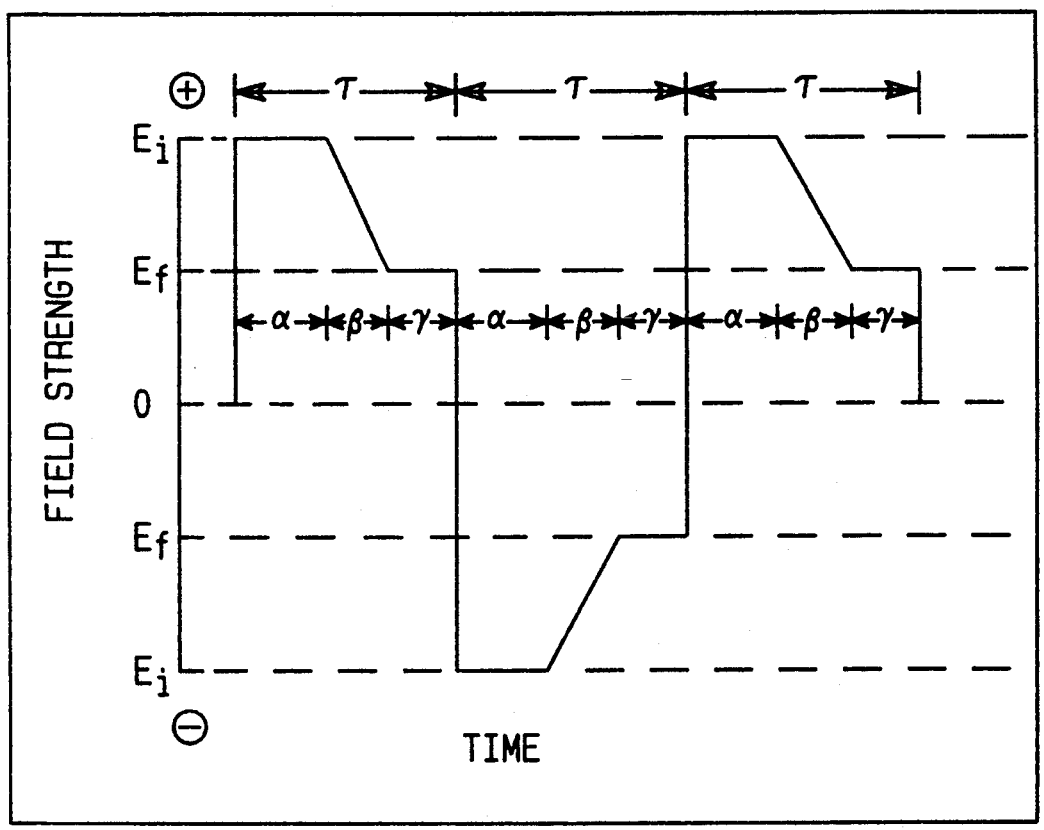
FIG. 4 is a graphic illustration of a generalized waveform of the electric field used to generate simulated fractograms in accordance with the invention.

FIG. 4 illustrates a generalized time-dependent waveform of the periodically reversed electric field, E, used to generate the simulated fractograms illustrated in the figures and described hereinafter. The electric field E is, of course, a function of time and the generalized waveform is characterized in that each half cycle, $\tau$, comprises three distinct phases, or time intervals, wherein:

$$\tau = \alpha + \beta + \gamma$$

and $\alpha$ represents the initial phase during which the electric field remained at a constant value, $E_i$; $\beta$ the secondary phase during which the field strength changed linearly to a final value, $E_f$; and $\gamma$ the final phase during which the field strength remains constant at $E_f$, prior to reversal of polarity.

$\alpha$, $\beta$, $\gamma$, and $\tau$ could all be treated as variables which could be assigned real number values or which could themselves be programmed as functions of time.

The assignment of real number values to $\alpha$, $\beta$ and $\gamma$ can result in a number of different waveform shapes. For instance, if $$\beta = \gamma = 0$$

then $$\tau = \alpha$$

and if $\alpha$ = a constant as a function of time, then $$E(t) = \pm E_i \text{ over each half cycle}$$

Figure 5:
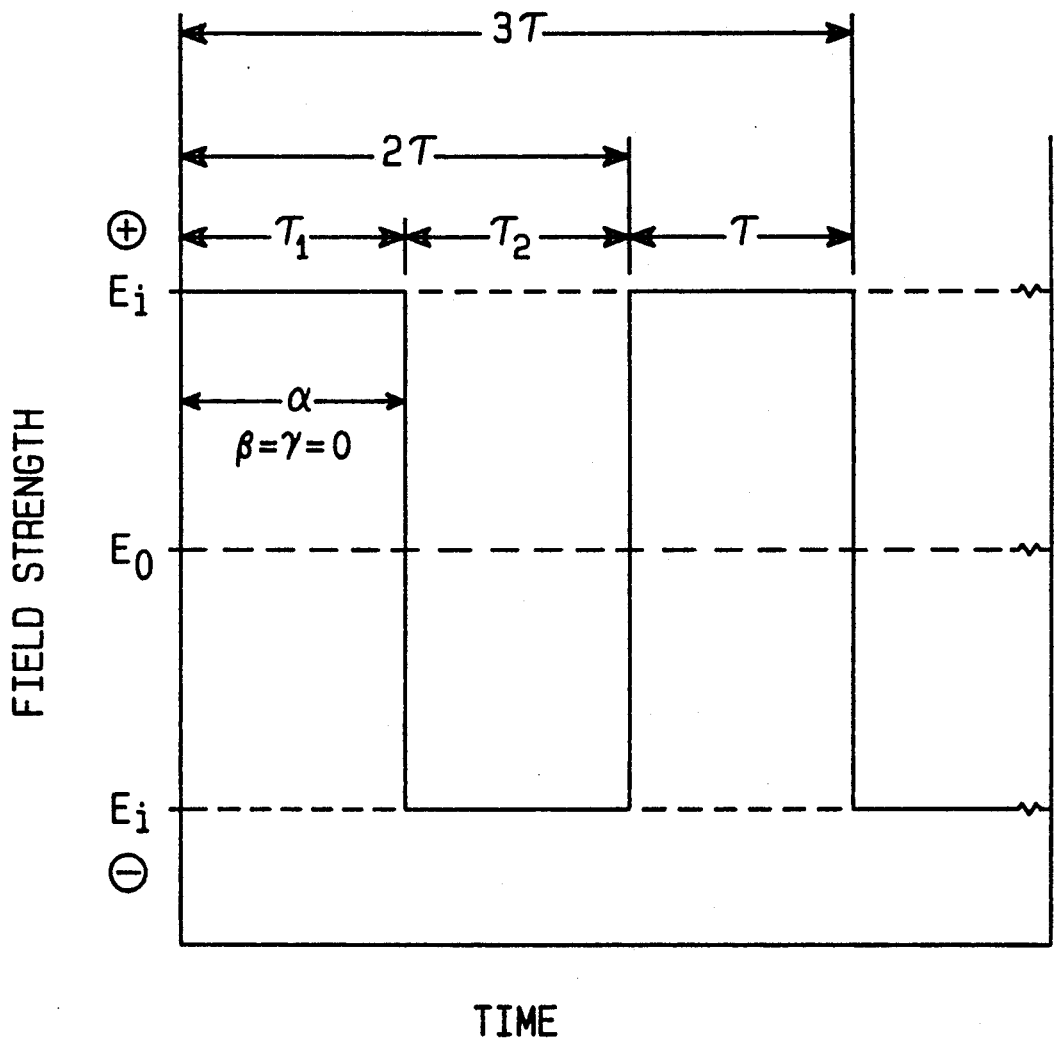
FIG. 5 is a graphic illustration of a standard square wave derived from the generalized waveform illustrated in FIG. 4.

This results in a standard square wave of constant frequency as illustrated in FIG. 5.

As another example, the period of the half cycle $\tau$ can vary as a function of an iterative cycle. For instance, if $\beta = \gamma = 0$ and n represents $n^{th}$ iterative cycle having a half cycle time period $\tau_n$ a total series of N oscillations, and $\tau_2 > \tau_1$ or $\tau_1 < \tau_2$ by a stipulated amount, then the expression $$\tau_n = \tau_1 + (\tau_2 - \tau_1) \cdot (n/N)^g$$

where g is a gradient factor, expresses a frequency-time function. If g=1, the frequency gradient for each half cycle is linear in nature and if g≠1, then a non-linear frequency time function results. For each of the simulated fractograms illustrated herein, g was assumed to be equal to unity.

Although the generalized electric field waveform depicted in FIG. 4 was used to generate the simulated fractograms disclosed herein, it will be understood that numerous other waveforms of the electric field E can be successfully employed. For instance, the electric field flow fractionation method of the present invention can be practiced utilizing a periodically reversing electric field E having a purely sinusoidal waveform, or may include a constant or variable amplitudes and/or frequencies and may even have discontinuities therein.

To generate the simulated fractograms illustrated herein, calculations were carried out as follows:

For any given solute j, the elution velocity (or rate of axial displacement) of the solute within the working chamber 13 can be given by the equation:

$$v_{e,j} = \frac{v_f \cdot t_{d,j}}{\tau}$$

in which $t_{d,j}$ is the time required for solute j to migrate toward the chamber wall 21 (transverse migration) and $v_f$ is the flow velocity of the carrier solvent. Thus, $t_{d,j}$ may be referred to as the axial displacement time, as axial displacement of solute j occurs during this interval. Time $t_{r,j}$ may be referred to as the residence time, or that period of time when solute j is substantially immobilized at the chamber wall 21. During $t_{r,j}$ axial transport is effected only by diffusion and may be considered negligible.

Therefore, any given half period of the electric field oscillation $\tau$ is comprised of the sum of $t_{d,j}$ and $t_{r,j}$.

The axial displacement time may also be derived from the electrophoretic velocity $v_{E,j}$ of solute j. The electrophoretic velocity is the velocity of solute j in the direction transverse to the flow of carrier solvent 31 and imparted to solute j by the electric field E. Thus, the axial displacement time $t_{d,j}$ is given by $$t_{d,j} = \frac{d}{v_{E,j}}$$

where $v_{E,j}$ is the electrophoretic velocity $$v_{E,j} = \mu_j E$$

and where $\mu_j$ is the electrophoretic mobility of solute j in the carrier solvent.

Because the strength of the electric field E can be expressed in terms of the voltage V applied to the electrical conductor plates 21, the elution velocity $v_{e,j}$ of any solute j can be directly calculated.

If the axial displacement time, $t_{d,j}$ is greater than or equal to one half period of oscillation, $\tau$, then the elution velocity, $v_{e,j}$, is equal to the flow velocity of the carrier solvent $v_f$.

If the axial displacement time $t_{d,j}$ is less than $\tau$ then $$v_{e,j} = v_f \cdot \frac{d^2 \epsilon / \mu_j V}{\tau}$$

While it is known that the flow velocity $v_f$ of the carrier solvent has a parabolic profile as illustrated in FIGS. 2A and 3A, for purposes of simplicity in the computer simulation of the fractograms, it is assumed that the flow rate is constant across the working chamber and zero at the chamber wall 21.

In the foregoing derivations, the electric field, E, was expressed as a constant during each half cycle $\tau$. That is to say, in terms of the generalized waveform illustrated in FIG. 4, $\tau$=a constant so that the above derivation and equations hold true for a standard square waveform as illustrated in FIG. 5.

If the generalized electric field waveform illustrated in FIG. 4 is used during fractionation, then the effect of the varying electric field must be calculated during each phase or time interval $\alpha$, $\beta$ and $\gamma$.

Although Eq. 1 still applies in this case, the calculation of $t_{d,j}$ is dependent upon which phase, $\alpha$, $\beta$, or $\gamma$, is associated with completion of the channel traverse by solute. If $d < Z_1$ where $$Z_1 = \mu_j E_i \alpha$$

represents the maximum distance traveled by solute j during the $\alpha$ phase, then $$t_{d,j} = \frac{d}{\mu_j \cdot E_i}$$

If $d < Z_2$, where $$Z_2 = Z_1 + \frac{\mu_j(E_i + E_f)}{2} \cdot \beta$$

represents the maximum distance traveled by solute j at the end of the $\beta$ phase, then $$t_{d,j} = \alpha - \frac{\mu_j \cdot E_i}{K} + \sqrt{\left(\frac{\mu_j E_i}{K}\right)^2 + \frac{2(d - Z_1)}{K}}$$

The choice of the positive value of the square root is dictated by the boundary condition that $t_{d,j} = \alpha$ if $d = Z_1$. In the above equation, K represents the rate of change of velocity of solute j during B phase:

$$K = \frac{\mu_j(E_f - E_i)}{\beta}$$

If $d < Z_3$, where $$Z_3 = Z_2 + \mu_j E_f \gamma$$

represents the maximum distance traveled at the end of phase, then $$t_{d,j} = \alpha + \beta + \frac{(d - Z_2)}{\mu_j E_f}$$

Finally, if $d = > Z_3$, then the elution velocity of the solute equals the flow velocity of the solvent.

In the computer algorithm used to generate simulated fractograms, the working chamber is considered to consist of a linear array of cells of equal volume. Transport of solute species is emulated by a Gaussian translation in which the mean represents the solute elution velocity as described above and the standard deviation represents dispersion. Standard deviations are weighted by the time required for transit between walls of the chamber.

Thus, an effective elution velocity for each solute may be calculated during each cycle of the iterative simulation, utilizing the frequency gradient as previously described, such that the periodicity of the electric field wave function changes during the course of a simulated run.

Because the chamber length is postulated to be 20 cm and its width, 1 cm, each cm of chamber represents a volume of 50 $\mu$L. A 50 $\mu$L sample occupies 5% of the chamber volume or 5 cells if the chamber is assigned 100 imaginary cells in the simulation. Assuming an arbitrary flow rate of 0.01 milliliters per minute, flow-through of the carrier solvent front requires 50 minutes or 100 iteration cycles. This then establishes an arbitrary carrier solvent flow rate of 1.0 cells per iterative cycle. Thus, each cycle represents 30 seconds. This elapsed time is sufficient to accommodate several oscillation cycles of the electric field at any of the frequencies specified in these examples and, thereby, justifies the use of average elution velocities.

Simulated fractograms were generated for isocratic frequency fields with periods ranging from 0.1 seconds to 0.9 seconds and are shown in FIG. 6. The periodically reversing electric field wave form is a square wave as $\beta=\gamma=0$ and the peak electric field was set as 1000 V/cm. Typical protein electrophoretic mobilities are in the range 0.1 to $1.0 \times 10^{-4}$ cm$^2$/V/second. In FIG. 6 the two solute molecules were assigned electrophoretic mobilities of $\mu_j = 5 \times 10^{-5}$ and $6 \times 10^{-5}$ cm$^2$/V/second, corresponding to transit times of 1.0 seconds and 0.84 seconds, respectively. For oscillation periods up to 0.85 seconds, the two solutes are not resolved and elute from the apparatus at the discharge end of the fractionating conduit with the solvent front. The elution profile obtained with $\tau = 0.85$ seconds is not identical to those obtained with shorter oscillation periods but is not graphically distinguishable. The perturbation that exists results from the dispersion of transit times and the existence of a subpopulation that, in fact, reaches the chamber wall.

For the purpose of these illustrations, the electric field strength is chosen arbitrarily. In the development of a working apparatus, the actual field strength will be determined by various engineering considerations, including (1) the maximum voltage differences sustained by a solvent of defined composition and thickness, and (2) the rate at which heat generated by electric field-induced current is dissipated. The underlying principle of the separation method described herein is not dependent upon the absolute value of field strength.

FIG. 6 shows that significant alteration of elution character is observed for $\tau = 0.9$ seconds, and with $\tau = 1.0$ second, two species are distinguished, the later elution peak representing the species of higher electrophoretic mobility. Resolution continues to rapidly increase with near-baseline separation obtained at $\tau = 1.3$ seconds. With increasing values of $\tau$, further separation of the two solute peaks is obtained, at the cost of peak broadening and increased elution time.

The effect of decreasing the magnitude of the electric field E, during the oscillation cycle, is depicted in the simulated fractograms shown in FIG. 7. The solute species are as in the previous figure, but with $\tau = 1.2$ seconds. In accordance with the generalized wave form depicted in FIG. 4, $\tau = 1.2$ seconds, $\beta = 0$ and therefore the field strength in the $\alpha$ phase is abruptly reduced to one-half its initial strength, with $E_i = 1000$ V/cm and $E_f = 500$ V/cm. For values of $\alpha > 0.85$, the elution behavior is insensitive to the decrease in field strength as the chamber transit of all solute molecules has been completed prior to this event. As $\alpha$ is further decreased, the resolution of the two species increases, without the increase in elution time and band spreading associated with increased $\tau$ above. Instead, elution time and band spreading are actually decreased. However, as $\alpha$ is further decreased, resolution between the eluted species is lost.

The optimal selection of $\alpha$ is determined by the time required for the more electrophoretically mobile component to cross the channel. A decrease in the electric field strength after this crossing has been completed results in a decrease in the electrophoretic velocity of the component remaining in transit, and therefore, increases the time in transit. As a result, the effective elution velocity or axial transport of the less mobile component is increased and the separation between the two peaks is enhanced. Loss of resolution with further decreasing of $\alpha$ occurs when $\alpha$ is too short in duration to permit completion of channel transit by the more electrophoretically mobile component.

Figures 9A, 9B, 9C, 9D, 9E:
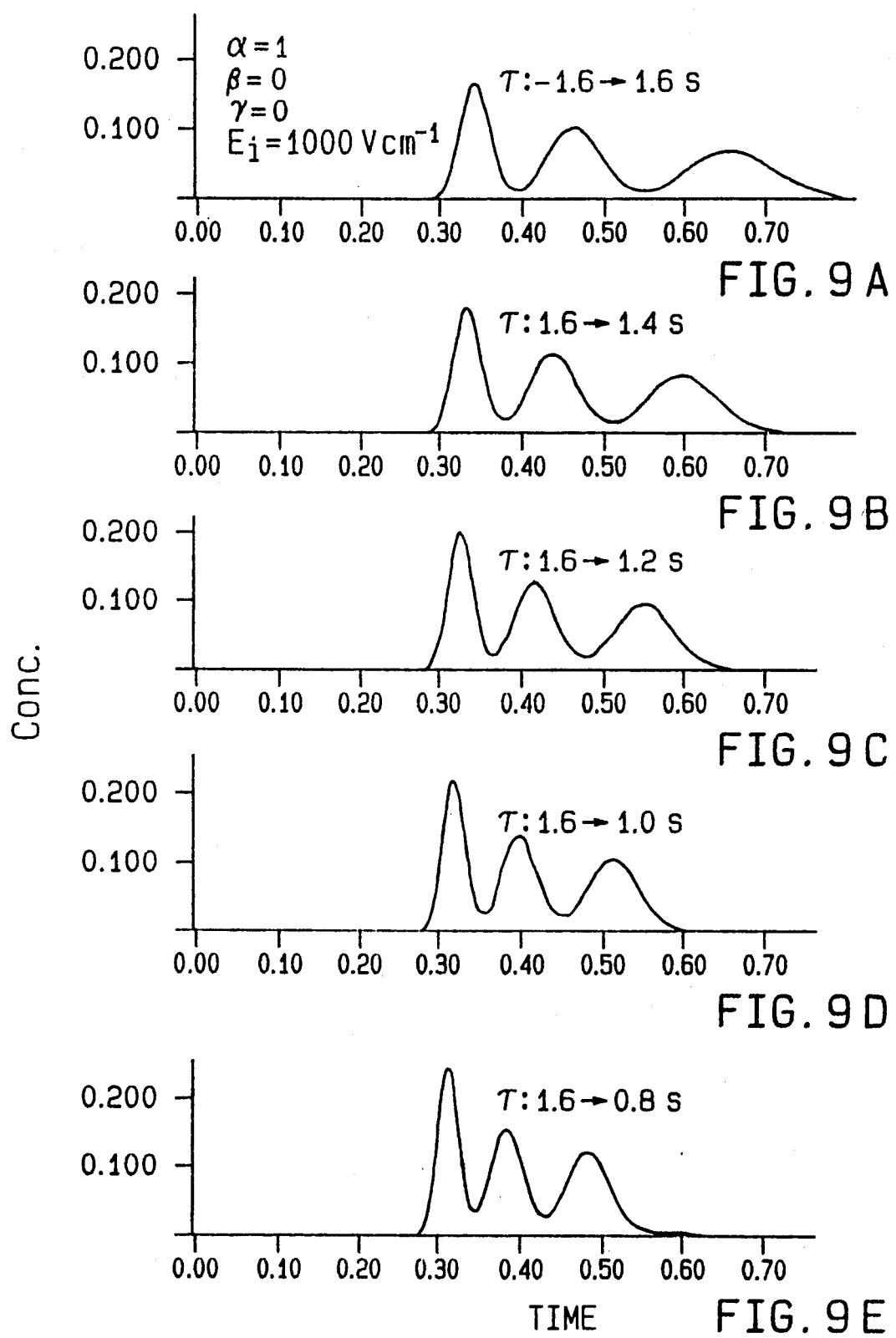

FIG. 8 illustrates fractionation of a ternary mixture in an isocratic frequency electric field in which a component of electrophoretic mobility $\mu_j = 7 \times 10^{-5}$ cm$^2$/V/second has been added to the binary mixture examined in FIGS. 6 and 7. As in FIG. 6, separation and elution of the solutes at the discharge end of the fractionating conduit is dependent upon the electric field waveform patterns. Separation between peaks improves with increased $\tau$ but band spreading and run length are also increased. At $\tau = 1.4$ seconds, the third component requires about 55% of the preset run time (400 cycles). As shown in FIG. 9, this time requirement increases to about 75% when $\tau$ is set at 1.6 seconds. However, separation of the bands to the baseline is essentially complete.

Additional fractograms in FIG. 9 illustrate the consequences of changing the electric field oscillation frequency during the execution of the run. Frequency decreases linearly during the course of the run. In the case of $\tau$ decreasing from 1.6 seconds to 0.8 seconds as a gradient, the time required for complete elution has decreased to 0.55% of the preset run time, comparable to the time requirement for the 1.4 seconds isocratic run (FIG. 8). However, compared to the 1.4 seconds isocratic run, less peak dilution has occurred with moderate loss of baseline separation.

Effectively, frequency (period) gradients are a means to combine in a single run oscillation periods optimal for separation of specific pairs of components in a multi-component mixture. Frequency gradients need not be linear; in partitioning of mixtures in which differences in electrophoretic mobility are not as uniform as in these examples, optimal separation can be expected to be achieved by gradients with periods that do not change uniformly in time. This process provides weighting of separation power appropriate to those pairs of components most similar in electrophoretic mobility (data not shown).

Ternary mixtures may also be separated by a biphasic voltage waveform as shown in FIG. 10. The components are as in FIGS. 6 and 7; $\tau$ is set at 1.2 seconds. The observed fractograms are insensitive to $\alpha$ for values of $\alpha \geq 0.85\tau$. As $\alpha$ is decreased to $0.70\tau$, separation between the two components that elute most rapidly from the apparatus is optimized. Additional decreases in the value of $\alpha$ improves the separation between the components that elute second and third, until baseline separation has been achieved for $\alpha = 0.60\tau$. However, resolution between the first two components has been lost.

In FIG. 11, an electric field waveform 'tuned' to achieve separation of all three components in a short run duration is shown. In these simulations, $\alpha$ is fixed at $0.60\tau$ while is varied from $0.0\tau$ to $0.30\tau$. It is noted that the positions of the first and third peaks are essentially unaffected by these changes. However, the position of the intermediate peak is highly sensitive to the value of $\beta$. Optimal separation is obtained for $\beta = 0.15-0.20\tau$.

The first peak in the fractograms depicted in FIG. 11 can be thought of as representing all components of mobility of $5 \times 10^{-5}$ cm$^2$/V/second or lower. The third peak can be thought of as representing the earliest elution position of all components of electrophoretic mobility of $7 \times 10^{-5}$ cm$^2$/V/second or higher. These results suggest that a partitioning system of this nature, by altering oscillation frequency and waveform, may be systematically modified to allow optimized purification of a single (electrophoretic) component in a complex mixture.

As demonstrated above, for $\tau >> t_{d,j}$, effective elution velocities are inversely related to electrophoretic mobility. If $\tau << t_{d,j}$, then the opposite relationship exists and elution velocity is directly related to electrophoretic mobility. The origin of these relationships was previously illustrated in FIGS. 2A–2F and 3A–3E.

Resolution of solutes by high-frequency electric field flow fractionation is a function of the solvent velocity function, $\tau$, and field strength. The 'steepness' of the solvent velocity parabola is a function of flow rate and distance between channel walls. The field strength and $\tau$ together determine the extent of axial penetration of the solute components in the carrier solvent. The combination of these three factors determines the difference in average axial velocities exhibited by the solutes, and hence, the resolution attained. The electric field cycle may be constructed of constant voltages of alternating polarity. Alternatively, a constant unidirectional field of moderate intensity might be spiked by short duration pulses of the opposite polarity to induce translation into the solvent stream. Because of the short cycle time, small differences in the time required by solutes to respond to the change in field polarity may make significant differences in effective elution velocity. Thus, two molecules of similar size, shape, and charge might be resolved if the charge distributions are such as to create significantly different dipole characteristics for the two molecules.

The embodiments of the invention in which an exclusive property or privilege is claimed are defined as follows:

1. A method of field flow fractionation for fractionating solute molecules from a solution, said method comprising the steps of:
   causing said solution to flow through a fractionating conduit, under conditions of laminar fluid flow, said fractionating conduit having an input end wherein said solution is introduced into said conduit and a discharge end wherein said solution and fractionated solute is removed from said conduit;
   applying an electric field across said flowing solution, between said input end and said discharge end of said conduit, said electric field having at least one vector component in a direction orthogonal to the direction of solution flow; and
   periodically reversing the polarity of said electric field while said solution flows through said conduit.

2. The method of claim 1, wherein said conduit comprises a pair of spaced-apart conductors separated by a pair of insulators and said electric field is applied by applying a voltage across said spaced-apart conductors.

3. The method of claim 2, wherein said pair of conductors is a pair of parallel plates and said conduit has an interior working chamber having a predetermined axial length, L, corresponding to the length of said plates and the direction of solution flow, said conduit having a substantially uniform rectangular transverse cross-sectional configuration having a predetermined width, W, and a predetermined depth, d, and wherein $L > W > d$.

4. The method of claim 3, wherein said electric field is substantially orthogonal to said plates.

5. The method of claim 1, wherein a plurality of compositions of solute molecules, each of said compositions of solute molecules having differing electrophoretic mobility in said solvent, are fractionated such that said compositions of solute molecules elute at substantially different times from the discharge end of said conduit.

6. The method of claim 5, wherein the frequency of said reversing polarity of said electric field is varied.

7. The method of claim 5, wherein said solute molecules are biological macromolecules.

8. A method of fractionating a plurality of differing compositions of solute molecules from a solution, said differing compositions of solute molecules having differing electrophoretic mobilities in said solution, said method comprising the steps of:
   causing said solution to flow through a fractionating conduit, under conditions of laminar flow, said fractionating conduit having an input end wherein said solution is introduced into said conduit and a discharge end wherein said solution and fractionated composition of solute molecules are removed from said conduit, and said conduit defining an interior working chamber having a predetermined axial length between a pair of opposing conduit walls;
   applying an electric field of a predetermined amplitude, A, across said flowing solution in said interior working chamber, said electric field having at least one vector component orthogonal to the direction of laminar solution flow; and
   periodically reversing the polarity of said electric field as a function of time so that said differing compositions of solute molecules elute from said discharge end of said conduit at different times under said conditions of laminar flow.

9. A method in accordance with claim 8 wherein said interior working chamber has a substantially uniform rectangular cross-sectional configuration transverse to the direction of said axial length, L, said cross-sectional configuration having a predetermined width W and a predetermined depth d and wherein $L>W>d$.

10. A method in accordance with claim 8 wherein said solution is diluted in a fluid carrier solvent, which carrier solvent, having said solution dissolved therein, flows through said conduit under conditions of laminar flow.

11. A method in accordance with claim 8 wherein said fractionated compositions of solute molecules are removed from said conduit at said discharge end in a time-dependent sequence, inversely related to the electrophoretic mobility of said compositions of said solute molecules.

12. A method in accordance with claim 8 wherein said fractionated compositions of solute molecules are removed from said conduit at said discharge end in a time-dependent sequence directly related to the electrophoretic mobility of said compositions of said solute molecules.

13. A method in accordance with claim 8 wherein the absolute value of said electric field amplitude varies as a function of time.

14. A method in accordance with claim 8 wherein said electric field is periodically reversed in a time-dependent manner of a waveform.

15. A method in accordance with claim 14 wherein the frequency of said waveform is varied.

16. A method in accordance with claim 14 wherein said waveform includes discontinuities.

17. A method in accordance with claim 15 wherein said frequency variation is nonlinear.

* * * * *